United States Patent
Brumfield et al.

(10) Patent No.: US 7,625,376 B2
(45) Date of Patent: Dec. 1, 2009

(54) REDUCING INSTRUMENT FOR SPINAL SURGERY

(75) Inventors: David L. Brumfield, Collierville, TN (US); Keith E. Miller, Germantown, TN (US)

(73) Assignee: Warsaw Orthopedic, Inc.

( * ) Notice: Subject to any disclaimer, the term of this patent is extended or adjusted under 35 U.S.C. 154(b) by 619 days.

(21) Appl. No.: 11/043,318

(22) Filed: Jan. 26, 2005

(65) Prior Publication Data
US 2006/0166534 A1 Jul. 27, 2006

(51) Int. Cl.
*A61F 5/00* (2006.01)
(52) U.S. Cl. .................................... 606/86 A
(58) Field of Classification Search .................. 606/61, 606/96, 99, 104, 205; 81/300
See application file for complete search history.

(56) References Cited

U.S. PATENT DOCUMENTS

| | | | |
|---|---|---|---|
| 3,604,487 A | 9/1971 | Gilbert | |
| 3,844,291 A | 10/1974 | Moen | |
| 4,411,259 A | 10/1983 | Drummond | |
| 5,020,519 A | 6/1991 | Hayes et al. | |
| 5,113,685 A | 5/1992 | Asher et al. | |
| 5,217,497 A | 6/1993 | Mehdian | |
| 5,314,431 A | 5/1994 | Graziano | |
| 5,330,472 A | 7/1994 | Metz-Stavenhagen | |
| 5,364,397 A * | 11/1994 | Hayes et al. | 606/61 |
| 5,389,099 A | 2/1995 | Hartmeister et al. | |
| 5,449,361 A | 9/1995 | Preissman | |
| 5,458,608 A | 10/1995 | Wortrich | |
| 5,466,243 A | 11/1995 | Schmieding et al. | |
| 5,474,555 A | 12/1995 | Puno | |
| 5,554,157 A | 9/1996 | Errico | |
| 5,616,143 A * | 4/1997 | Schlapfer et al. | 606/61 |
| 5,647,873 A | 7/1997 | Errico | |
| 5,690,630 A | 11/1997 | Errico | |
| 5,720,751 A | 2/1998 | Jackson | |
| 5,782,830 A | 7/1998 | Farris | |
| 5,810,878 A | 9/1998 | Burel et al. | |
| 5,817,094 A | 10/1998 | Errico | |
| 5,863,293 A | 1/1999 | Richelsoph | |
| 5,899,901 A | 5/1999 | Middleton | |
| 5,910,141 A | 6/1999 | Morrison et al. | |
| 5,944,720 A | 8/1999 | Lipton | |
| 5,964,760 A | 10/1999 | Richelsoph | |
| 6,010,503 A | 1/2000 | Richelsoph | |
| 6,036,692 A | 3/2000 | Burel et al. | |

(Continued)

FOREIGN PATENT DOCUMENTS

DE 4238339 A1 5/1994
WO WO 93/11715 A 6/1993

*Primary Examiner*—Thomas C Barrett
*Assistant Examiner*—Nicholas Woodall (57) ABSTRACT

An instrument is provided for use in orthopedic surgery for reduction of a connecting member such as a spinal rod toward an implant such as a bone screw. An embodiment of the instrument includes handle portions that are pivotable relative to each other and biased apart, and arm portions pivotable relative to each other and to the handle portions. Distal portions of the arm portions, which are offset from the arm portions, provide structure for engaging a connecting member and an implant. Squeezing the handle portions force the distal portions of the arm portions together, forcing together the connecting member and the implant. A toothed bar and pawl may be provided to retain the instrument in a squeezed state.

38 Claims, 7 Drawing Sheets

U.S. PATENT DOCUMENTS

| | | | |
|---|---|---|---|
| 6,042,582 | A | 3/2000 | Ray |
| 6,063,088 | A | 5/2000 | Winslow |
| 6,355,040 | B1 | 3/2002 | Richelsoph |
| 6,440,133 | B1 * | 8/2002 | Beale et al. .................. 606/61 |
| 6,440,137 | B1 | 8/2002 | Horvath et al. |
| 6,443,953 | B1 | 9/2002 | Perra et al. |
| 6,471,705 | B1 | 10/2002 | Biedermann et al. |
| 6,520,963 | B1 | 2/2003 | McKinley |
| 6,530,929 | B1 * | 3/2003 | Justis et al. ................. 606/103 |
| 6,551,316 | B1 * | 4/2003 | Rinner et al. ................. 606/57 |
| 6,565,565 | B1 | 5/2003 | Yuan et al. |
| 6,648,888 | B1 | 11/2003 | Shluzas |
| 6,660,006 | B2 | 12/2003 | Markworth et al. |
| 6,695,843 | B2 | 2/2004 | Biedermann et al. |
| 6,726,692 | B2 | 4/2004 | Bette |
| 6,746,449 | B2 * | 6/2004 | Jones et al. .................... 606/61 |
| 6,755,829 | B1 | 6/2004 | Bono et al. |
| 6,843,791 | B2 | 1/2005 | Serhan |
| 7,008,422 | B2 * | 3/2006 | Foley et al. ............... 623/17.16 |
| 2002/0072752 | A1 * | 6/2002 | Zucherman et al. ........... 606/99 |
| 2003/0225408 | A1 | 12/2003 | Nichols et al. |
| 2004/0049191 | A1 | 3/2004 | Markworth et al. |
| 2004/0138662 | A1 | 7/2004 | Landry et al. |
| 2004/0147936 | A1 * | 7/2004 | Rosenberg et al. ............ 606/99 |
| 2004/0172022 | A1 | 9/2004 | Landry et al. |
| 2004/0193160 | A1 | 9/2004 | Richelsoph |
| 2004/0249378 | A1 * | 12/2004 | Saint Martin et al. ......... 606/61 |
| 2005/0154389 | A1 | 7/2005 | Selover et al. |
| 2005/0171540 | A1 * | 8/2005 | Lim et al. ..................... 606/61 |
| 2005/0192587 | A1 | 9/2005 | Lim |
| 2006/0025768 | A1 * | 2/2006 | Iott et al. ...................... 606/61 |
| 2006/0166535 | A1 * | 7/2006 | Brumfield et al. ........... 439/179 |

* cited by examiner

REDUCING INSTRUMENT FOR SPINAL SURGERY

BACKGROUND

In orthopedic surgical procedures, it is known to implant devices to support bones or other tissue, to correct deformities, to hold tissues in position for healing after injuries or other surgery, and for other purposes relating to orthopedic health. For example, where correction of a scoliotic or other abnormal curvature or misalignment of the spine is desired, a sturdy rod, plate, or other elongated connecting member can be placed along one or more vertebral segments to support or hold the segments in a corrected position. Bone screws, bone hooks or other fixation implants are attached to vertebrae and connected to the connecting member to secure the connecting member along the spinal column.

Commonly, the fixation implants and the connecting member(s) are placed separately, that is, they are not connected together prior to implantation in the body. For example, bone screws may be implanted into vertebrae first, connectors may be placed on or around the screws (if necessary), and then the connecting member may be placed into the body. The connecting member may be contoured prior to insertion to approximate the curvature desired, or it may be contoured after placement adjacent the spine. In cases where a connecting member and bone screws or other fixation elements are separately placed, the connecting member and screws may be required to be forced toward each other for connection. The process of moving the connecting member and fixation elements toward each other for connection is generally termed "reduction."

Reduction can be accomplished by hand, although the environment and close quarters of a surgical site can make reduction by hand quite difficult. While instruments have been developed to provide a mechanical advantage in reducing or positioning the connecting member relative to an anchor, there remains a need for reducing instruments which are maneuverable relative to the anchor and connecting member to facilitate insertion and manipulation of the connecting member and anchor through the incision or portal in which the reducing instrument is positioned.

DESCRIPTION OF THE ILLUSTRATED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device, and any such further applications of the principles of the invention as illustrated herein, are contemplated as would normally occur to one skilled in the art to which the invention relates.

Referring generally to the figures, there is shown a reducing instrument 20 that is removably engageable to an implant (e.g. a bone screw or other anchor) and operable to move a rod or other elongated connecting member and the implant toward each other. Reducing instrument 20 includes handle portions 22 and 24, springs 26 and 28, and arm portions 30 and 32. Use of instrument 20 allows good visibility of the implant and remote or sideward positioning of the reducing instrument in alignment with the implant.

Handle portion 22 is generally elongated, having a generally proximal end 40 and a generally distal end 42. Proximal end 40 may be pivotally connected to a toothed bar 44. Toothed bar 44 may be pivotally connected at 46 to a ratchet post 48, having a slot 49, which is pivotally connected to proximal end 40 of handle portion 22. Handle portion 22 may also have a thickened portion 50 to provide a guide for the surgeon's hand, to provide a more stable or secure connection to bar 44 and/or ratchet post 48 if they are present, or for other purposes. Handle portion 22 also includes hole 52 through which handle portion 22 can be connected to handle portion 24. Hole 52 is formed through a part-circular portion 53 that extends from an inside surface of handle portion 22. Portion 53 is thinner than handle portion 22 and is substantially centered on handle portion 22. Hole 52 is generally between proximal end 40 and distal end 42; in the illustrated embodiment hole 52 is relatively close to or adjacent distal end 42. A forked portion 54 is provided at distal end 42, for connecting to an arm portion, as further described below. Forked portion 54 includes holes 55a and 55b, one of which (e.g. 55a) may be threaded.

Handle portion 24 is generally elongated, having a generally proximal end 60 and a generally distal end 62. Proximal end 60 may include a pawl 64 for engaging toothed bar 44. Further, a release lever 66 having a handle 68 and a contact surface 70 may be pivotally connected to proximal end 60. Pressing on handle 68 causes lever 66 to pivot so that contact surface 70 pushes against bar 44 to disengage bar 44 from pawl 64, allowing handle portions 22 and 24 to be spaced apart. Handle portion 24 also includes a groove 72 that makes distal end 62 generally divided or forked. Holes 74a and 74b through which handle portion 24 can be connected to handle portion 22 are provided generally between proximal end 60 and distal end 62, and in the illustrated embodiment adjacent distal end 62. Holes 74a and 74b are formed through part-circular portions 76a and 76b that extend from an inside surface of handle portion 24. Forked distal end 62 also includes holes 78*a* and 78*b* for connecting to an arm portion, as further described below. One or both of holes 78*a* and 78*b* (e.g. 78*a*) may be threaded.

In the illustrated embodiment, two leaf springs 26 and 28 are provided to bias handle portions 22 and 24 apart. Spring 26 is attached at or adjacent to an end 90 to handle portion 22 relatively close to proximal end 40, as by a set screw 91 or other connector. Spring 28 is attached at or adjacent to an end 92 to handle portion 24 relatively close to proximal end 60, as by a set screw 91 or other connector. Springs 26 and 28 may interengage, for example via a tongue-and-groove type of engagement. In that configuration, spring 26 may have a tongue portion 94 at the end opposite end 90, and spring 28 may have a groove 96 at the end opposite end 92. When springs 26 and 28 are attached to handle portions 22 and 24, tongue 94 extends into and/or through groove 96. In one particular embodiment, spring 26 may have a tab 98 at or adjacent to end 90 that can be inserted in slot 49 of ratchet post 46. Tab 98 acts as a spring to apply a force on bar 44 to maintain bar 44 in contact with pawl 64. It will be seen that only one leaf spring, such as spring 26 (with or without tongue 94 or tab 98) may be provided for biasing handle portions 22 and 24 apart, or one or more coil or other springs may be provided, or other appropriate structure for biasing handle portions 22 and 24 apart.

Arm portion 30 is an elongated piece having a proximal end 110 and a distal end 112. A relatively thin part-circular portion 114 is provided at or adjacent proximal end 110 with a hole 116 for connecting to hole 54 of handle portion 22. Arm portion 30 also includes a grooved or forked portion 118 generally between proximal end 110 and distal end 112 and in the illustrated embodiment adjacent proximal end 112. Holes 120*a* and 120*b* through which arm portion 30 can be connected to arm portion 32 are provided in forked portion 118. Holes 120*a* and 120*b* are formed through part-circular portions 121*a* and 121*b* that extend from an inside surface of arm portion 30. One or both of holes 120*a* and 120*b* (e.g. 120*a*) may be threaded.

Distal end 112 has a substantially U-shaped portion 122 having extension portions 124 and 126 and cross-pieces 128 and 130. In the illustrated embodiment, extension portions 124 and 126 are substantially parallel to each other, and are substantially perpendicular to cross-pieces 128 and 130. Cross piece 128, in one embodiment, is essentially a lateral extension of the main part of arm portion 30. Cross-piece 130 may include a tab 132 generally extending toward cross-piece 128, which may be at least partially curved, e.g. to provide a surface with a curvature approximating that of an orthopedic rod. Extension portions 124 and 126 include substantially part-cylindrical hollows 134 and 136, respectively. Hollows 134 and 136 are linear, i.e. the axes of the cylinders of which hollows 134 and 136 are a part are collinear, and hollows 134 and 136 may be of a size and curvature to accommodate an orthopedic rod, e.g. forming a substantially semi-circular (180-degree) section. In a particular embodiment, arm portion 30 has a longitudinal axis L. U-shaped portion 122 is laterally offset from axis L, and may be offset in a direction substantially perpendicular to axis L. U-shaped portion 122 may also be angled with respect to axis L, in a particular embodiment so that U-shaped portion 122 bends toward arm portion 32. Such an angle α may be about 160 degrees in one embodiment.

Arm portion 32 is an elongated piece having a proximal end 140 and a distal end 142. A relatively thin part-circular portion 144 is provided at or adjacent proximal end 140 with a hole 145 for connecting to holes 78*a* and 78*b* of handle portion 24. Arm portion 30 also includes another relatively thin part-circular portion 146 with a hole 148 generally between proximal end 140 and distal end 142 and extending from an inside surface of arm portion 32, and in the illustrated embodiment adjacent proximal end 142. Portion 146 fits within forked portion 118 of arm portion 30 so that hole 148 communicates with holes 120*a* and 120*b*.

Distal end 142 has a substantially U-shaped portion 152 having extension portions 154 and 156 and cross-piece 158. In the illustrated embodiment, extension portions 154 and 156 are substantially parallel to each other, and are substantially perpendicular to cross-piece 158. Cross piece 158, in one embodiment, is essentially a lateral extension of the main part of arm portion 32. Extension portions 154 and 156 include protrusions 160 and 162 that may be substantially cylindrical. Protrusions 160 and 162 may be substantially linear, i.e. the axes of protrusions 160 and 162 are collinear, and may be relatively thin or short. Protrusions 160 and 162 are for connecting to indentations or hollows in an implant, and therefore they may be configured to accommodate the shape, depth and/or other features of such indentations or hollows.

In a particular embodiment, arm portion 32 has a longitudinal axis M. U-shaped portion 152 can be laterally offset from axis M, and may be offset in a direction substantially perpendicular to axis M. As with portion 122 of arm 30, U-shaped portion 152 could also be angled with respect to axis M in another plane.

Figure 3:
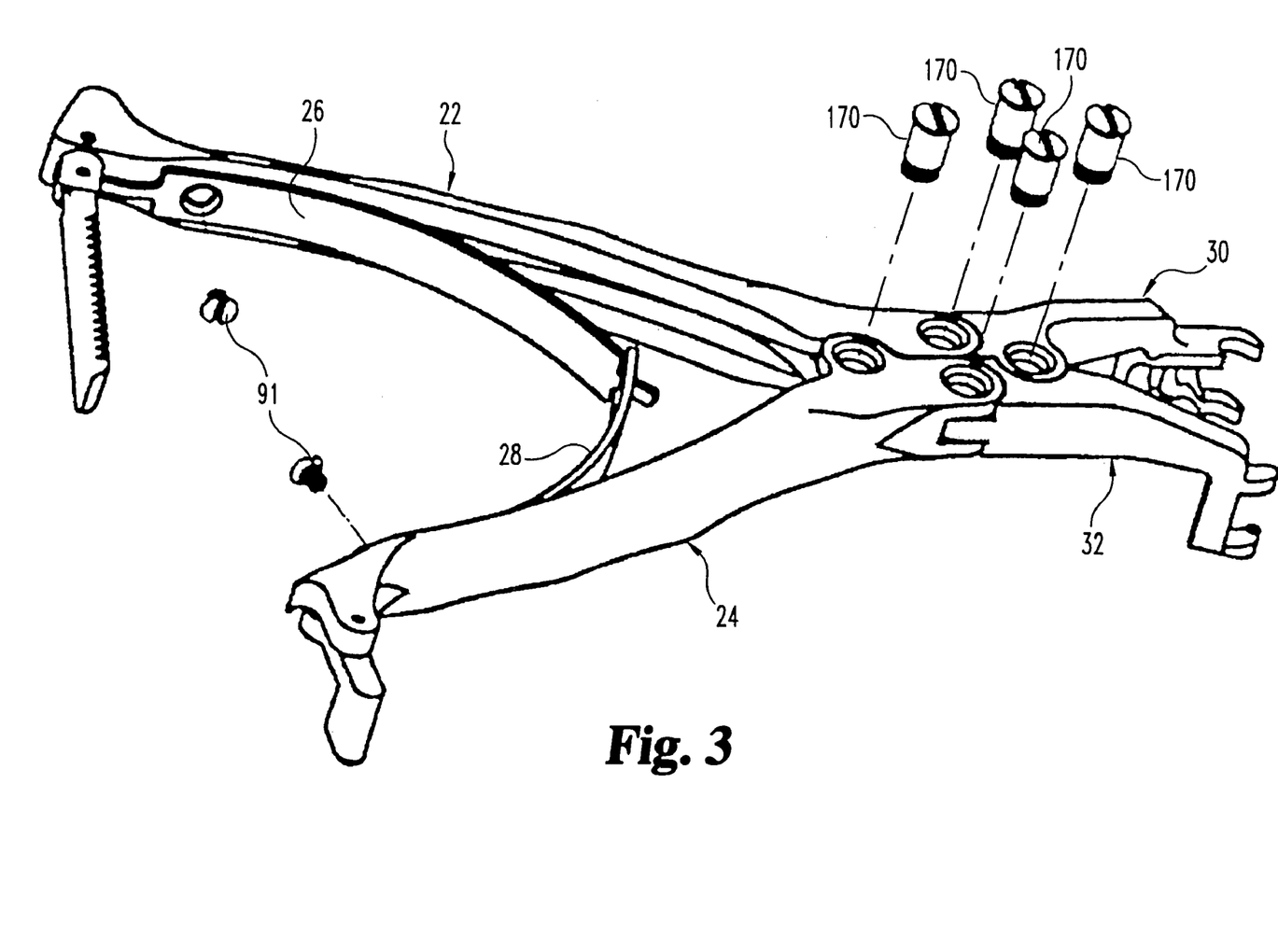
FIG. 3 is another view of the embodiment shown in FIG. 1 in substantially a reverse perspective from that shown in FIG. 1, with certain parts shown in exploded fashion.
Figure 4:
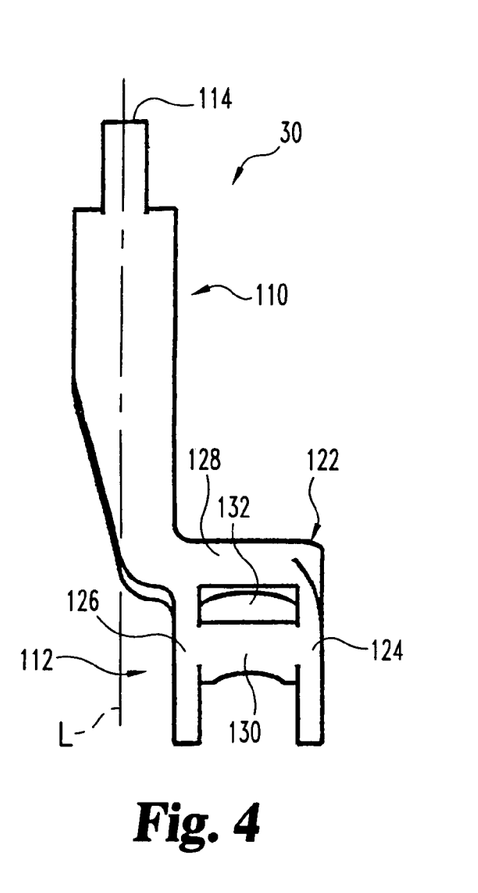
FIG. 4 is a top plan view of an embodiment of an arm portion of the embodiment shown in FIG. 1.
Figures 5, 6:
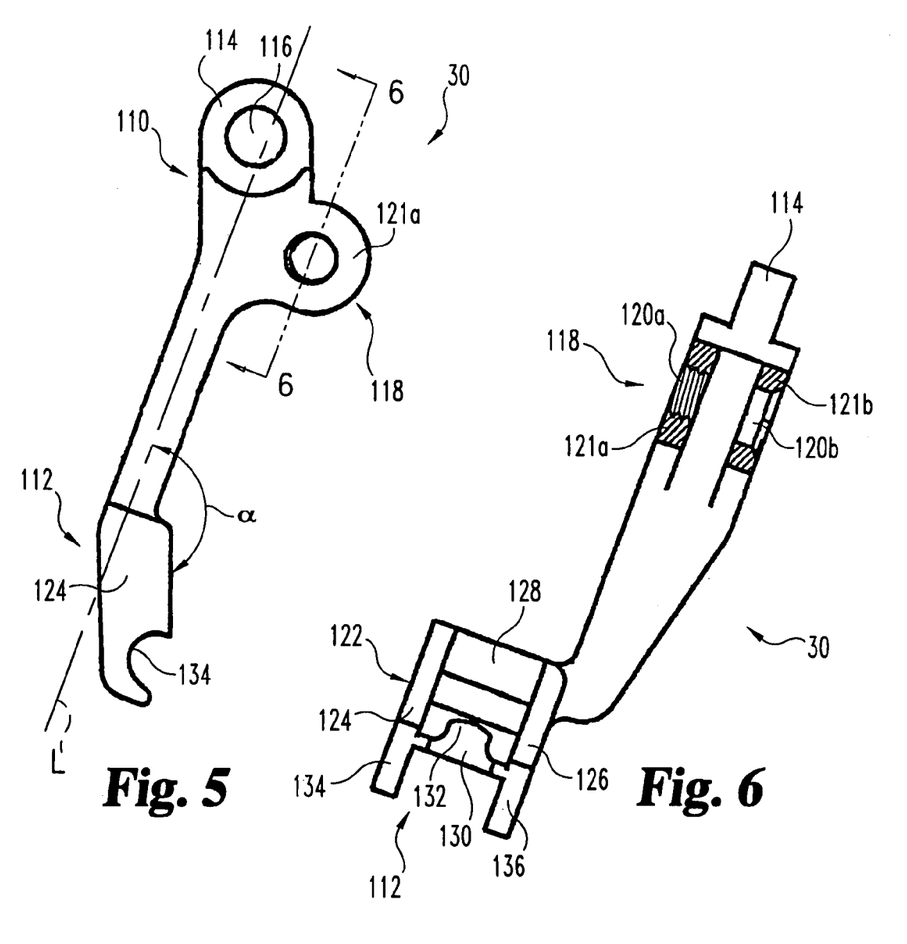
FIG. 5 is a side plan view of the embodiment shown in FIG. 4.
FIG. 6 is a partial cross-sectional view of the embodiment shown in FIG. 4, taken along the line 6-6 in FIG. 5 and viewed in the direction of the arrows.
Figures 7, 8, 9:
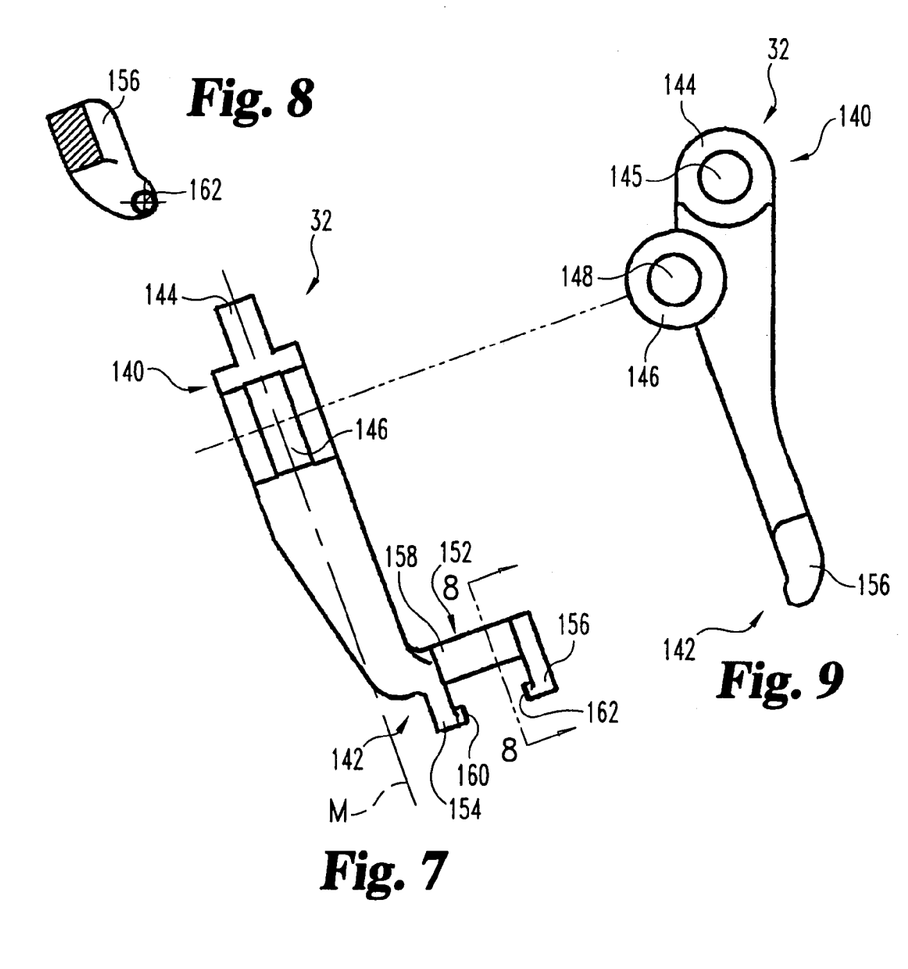
FIG. 7 is a top plan view of an embodiment of an arm portion of the embodiment shown in FIG. 1.
FIG. 8 is a cross-section view of the embodiment shown in FIG. 7, taken along the line 8-8 in FIG. 7 and viewed in the direction of the arrows.
FIG. 9 is a side plan view of the embodiment shown in FIG. 7.
Figure 10:
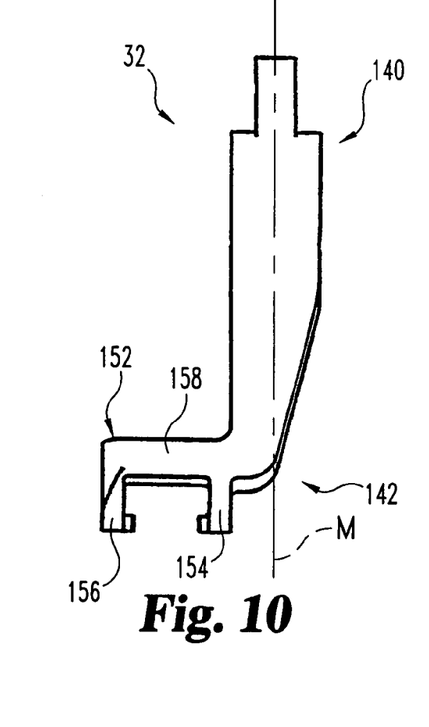
FIG. 10 is a bottom plan view of the embodiment shown in FIG. 7.

As has been suggested above, instrument 20 is assembled generally as follows. Handle portions 22 and 24 are connected by inserting thin portion 53 of handle portion 22 into grooved portion 72 of handle portion 24 so that hole 52 of handle portion 22 communicates with holes 74*a* and 74*b* of handle portion 24. An axle, for example a rivet, pin or set screw (e.g. set screws 170 in FIG. 3), can be inserted through holes 52, 74*a* and 74*b* and secured so that handle portions 22 and 24 can pivot with respect to each other around such an axle. In an embodiment in which at least one of holes 52, 74*a* and 74*b* are at least partially threaded, a set screw may be used as the axle, with the relative advantage that the interacting threads tend to retain the set screw within the holes. In other embodiments, a separate retaining piece, such as a ring to fit into a groove of an axle, or an additional step to retain the axle within the holes, such as swaging or peening part of the axle, can be included.

It will be seen that connection of handle portions 22 and 24 should account for connections of associated parts that may be present. For example, in embodiments in which handle portion 22 includes toothed bar 44 and handle portion 24 includes pawl 64, connection of handle portions 22 and 24 should ensure that bar 44 and pawl 64 connect. In embodiments including lever 66, lever 66 should be proximate to or abut bar 44. As another example, in embodiments in which handle portions 22 and/or 24 include springs, connection of handle portions 22 and 24 should ensure that the one or more springs are proximate to or abut each other or the opposing handle portion so that biasing apart of the handle portions 22 and 24 occurs. In one particular embodiment, as noted above leaf springs 26 and 28 should be arranged so that tongue 94 of spring 26 is at least partially within groove 96 of spring 28.

Arm portions 30 and 32 are connected to each other, and each is connected to one of the handle portions 22 and 24, substantially as described above. Thin portion 146 of arm portion 32 is inserted into grooved portion 118 of arm portion 30 so that hole 148 of arm portion 32 communicates with holes 120*a* and 120*b* of arm portion 30. An axle as described above can be inserted through holes 148, 120*a* and 120*b* and secured so that arm portions 22 and 24 can pivot with respect to each other around such an axle. A set screw (e.g. set screws 170 in FIG. 3) may be used as such an axle, particularly in embodiments in which at least one of holes 148, 120a and 120b are at least partially threaded. Arm portion 30 is connected to handle portion 22 by inserting thin portion 114 of arm portion 30 into the forked end 54 of handle portion 22, so that hole 116 of arm portion 30 communicates with holes 55a and 55b of handle portion 22. An axle as described above can be inserted through holes 116, 55a and 55b and secured so that arm portion 30 and handle portion 22 can pivot with respect to each other around such an axle. A set screw (e.g. set screws 170 in FIG. 3) may be used as such an axle, particularly in embodiments in which at least one of holes 116, 55a and 55b are at least partially threaded. Arm portion 32 is connected to handle portion 24 by inserting thin portion 144 of arm portion 32 into the forked end of handle portion 24, so that hole 145 of arm portion 32 communicates with holes 78a and 78b of handle portion 24. An axle as described above can be inserted through holes 145, 78a and 78b and secured so that arm portion 32 and handle portion 24 can pivot with respect to each other around such an axle. A set screw (e.g. set screws 170 in FIG. 3) may be used as such an axle, particularly in embodiments in which at least one of holes 145, 78a and 78b are at least partially threaded.

Figure 1:
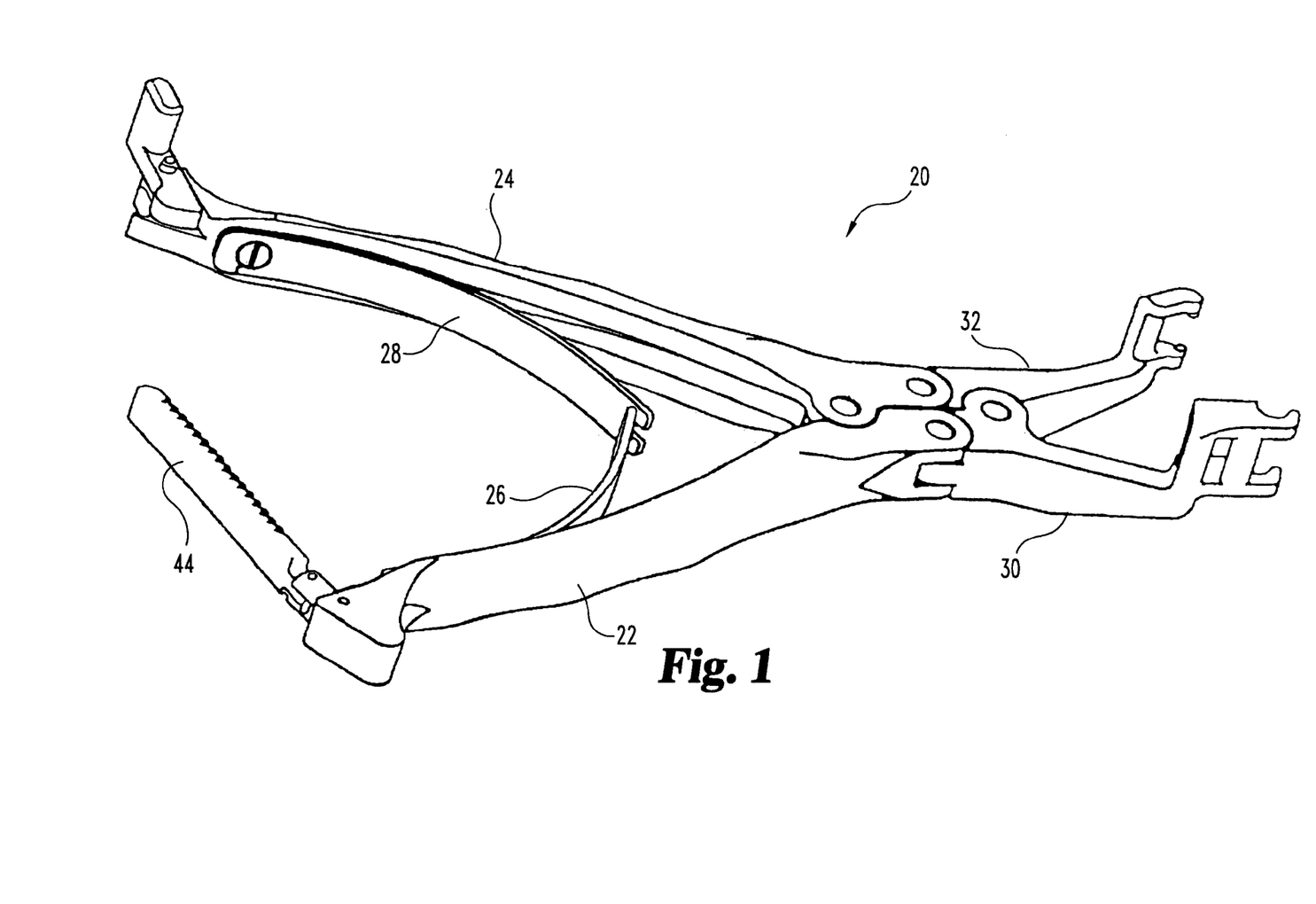
FIG. 1 is a perspective view of an embodiment of an instrument according to the present invention.
Figure 2:
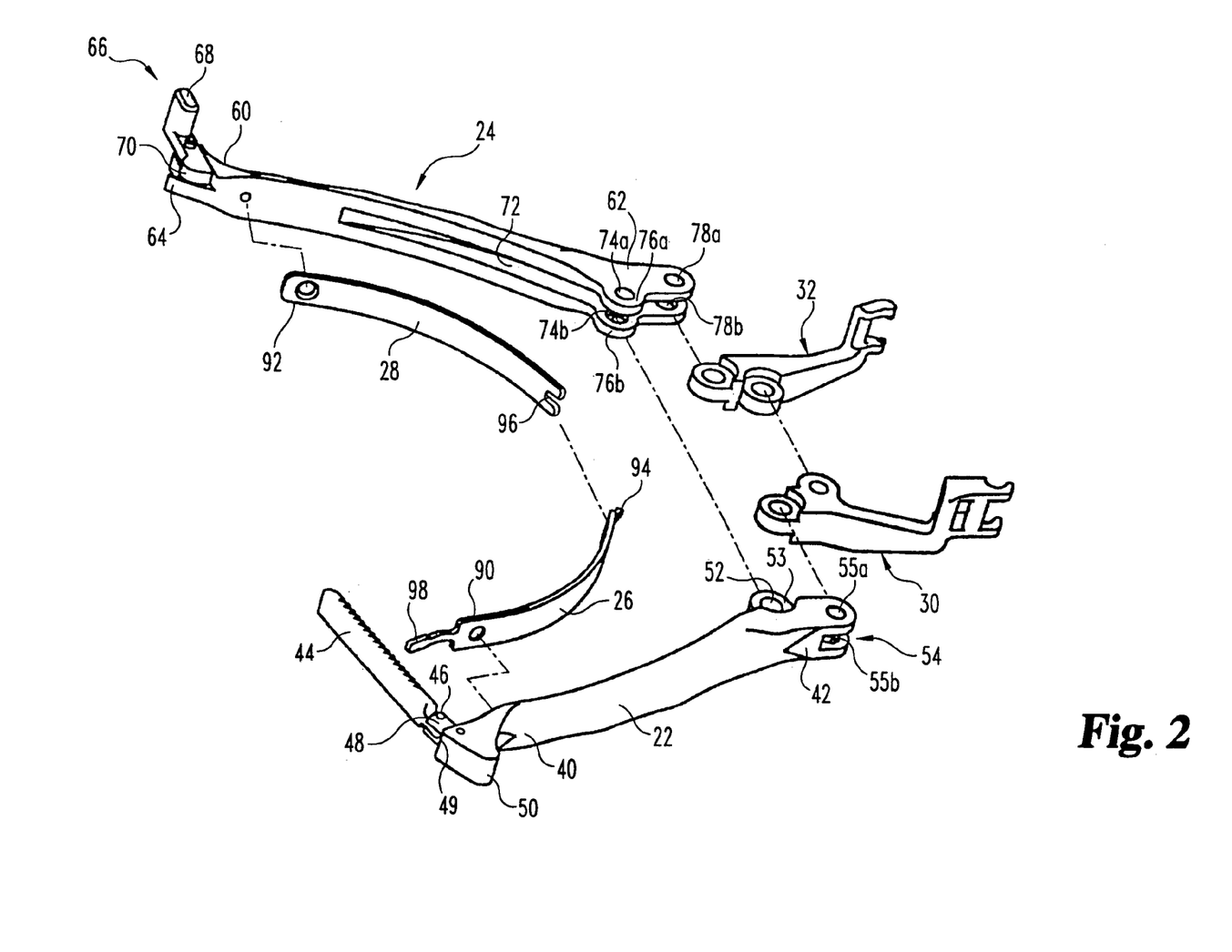
FIG. 2 is an exploded perspective view of the embodiment shown in FIG. 1.

It will be seen that the several portions of embodiments of instrument 20 can be connected in a variety of orders. For example, arm portions 30 and 32 can be connected to each other, then to individual handle portions 22 and 24, with the final connection being that between handle portions 22 and 24. As another example, handle portions 22 and 24 can be connected together first, then to arm portions 30 and 32, with arm portions 30 and 32 being either separate or already connected. The instrument 20 can be assembled as indicated above and in FIGS. 1-3, with distal portions 112 and 142 of arms 30 and 32 offset to the left when handle portion 22 is substantially atop handle portion 24. That positioning occurs when handle portion 22 is directly connected to arm 30 and handle portion 24 is directly connected to arm 32. Instrument 20 can also be assembled so that arm 30 is directly connected to handle portion 24, and arm 32 is directly connected to handle portion 22. In that case, distal portions 112 and 142 of arms 30 and 32 are offset to the left when handle portion 24 is substantially atop handle portion 22, as in FIGS. 11-12.

In using the illustrated embodiment of instrument 20, it will be seen that squeezing handle portions 22 and 24 together causes rotation of handle portions 22 and 24 with respect to each other, so that their respective distal ends 42 and 62 move apart. As distal ends 42 and 62 move apart, the proximal parts of arm portions 30 and 32 also move apart. By virtue of the pivoting connection of arm portions 30 and 32, when the proximal parts of arm portions 30 and 32 move apart, their respective distal portions 112 and 142 move together. Thus, by squeezing handle portions 22 and 24 together, the distal portions 112 and 142 are forced together.

The operation of instrument 20 to engage an implant and rod or other connecting member and seat the connecting member in the implant anchor will now be described with respect to operation on a spinal column. Alternative uses with respect to other bony structures or other tissues can be made. As with other types of orthopedic surgery, an incision is made and access is gained to the surgical site. The approach to the surgical site can be an open approach, i.e. a relatively long incision with retraction of underlying tissue. The instrument disclosed herein can be used in such an approach, or with other surgical techniques.

After access to the surgical site has been obtained, anchors such as those including a receiver member 180 are inserted into bone tissue. Such anchors may be pre-fitted with receiver member 180 or other receiver member embodiment, and such anchors typically include a bone engaging portion 182 and a channel 183 for accommodating part of rod R. Such a channel 183 may point substantially to the side as shown in the figures, or may open to the back of the anchor, or be otherwise oriented. Such receiver members may also be placed on or over engaging portions after engagement of the engaging portions into bone, and may be multi-axial, pivotable or otherwise adjustable with respect to such engaging portions. A connecting member, such as rod R, is inserted into the surgical site, and placed adjacent one or more of the anchors. If not already present, receiver members 180 may be loosely placed on the connecting member prior to insertion of the connecting member to the surgical site. The anchors and connecting member are manipulated so that a part of the connecting member is in or near the each of the anchors. Receiver member 180 can include a pair of branches 184 which generally form channel 183 therebetween. Instrument 20 may be used with a variety of anchors or implants, including those known previously in the art and those disclosed in U.S. patent application Ser. Nos. 11/000,585 (published as U.S. Patent Application Publication No. 2006/0116687 and filed on Nov. 30, 2004) and 11/000,846 (published as U.S. Patent Application Publication No. 2006/0116677 and filed on Dec. 1, 2004), respectively entitled SIDE-LOADING ADJUSTABLE BONE ANCHOR and SIDE-LOADING BONE ANCHOR, which are incorporated herein by reference in their entireties.

After engagement of the implant to a vertebra, rod R is positioned adjacent the implant. It is contemplated that a number of implants can be positioned and engaged along the spinal column, and the rod engaged in a channel or other area of one of the implants. Due to misalignment of vertebrae, misalignment of the implants, or other conditions, the rod may not be easily or readily positioned in one or more implants.

Figure 11:
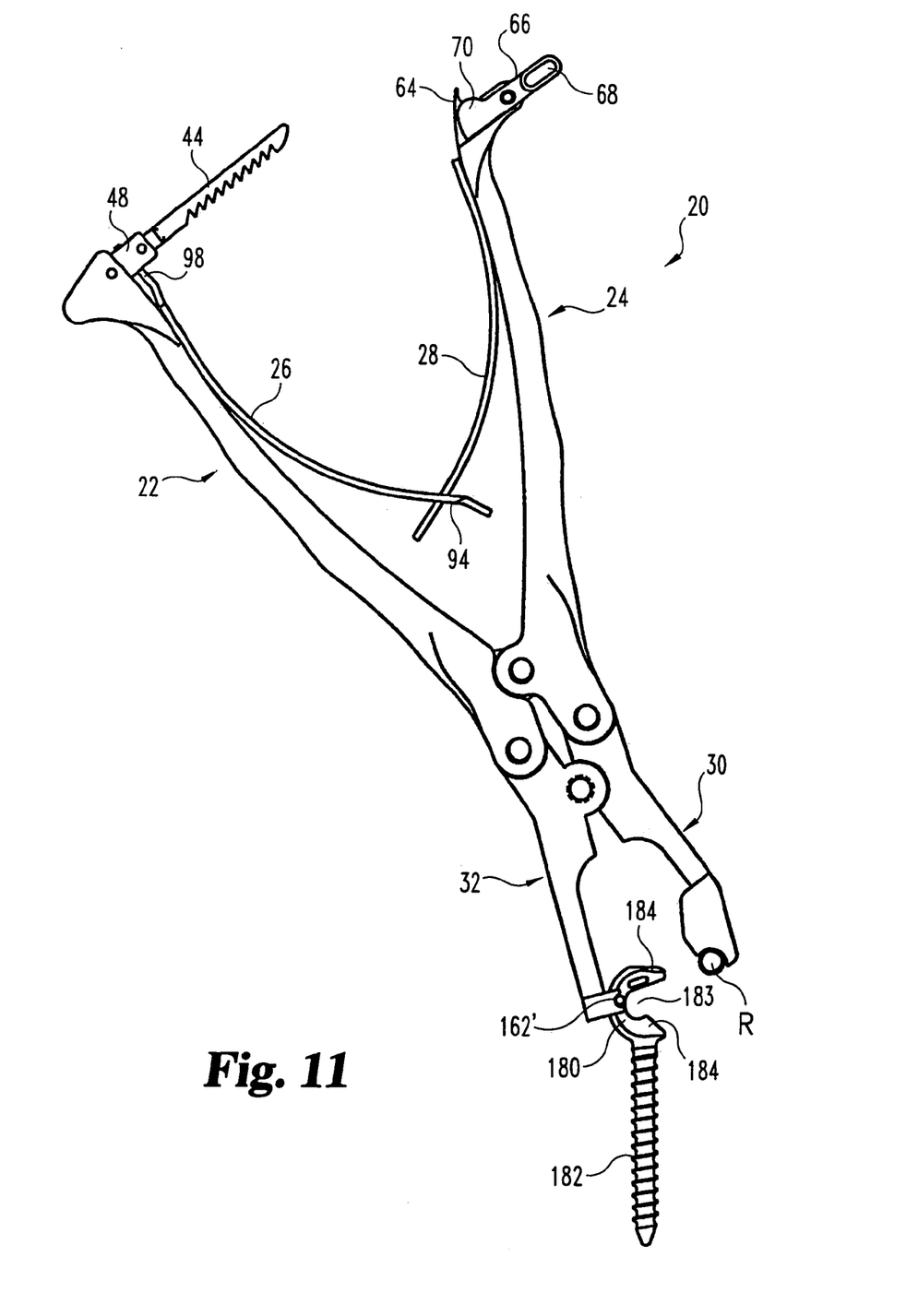
FIG. 11 is a side view of an embodiment of an instrument in relation to an orthopedic rod and an orthopedic implant.
Figure 12:
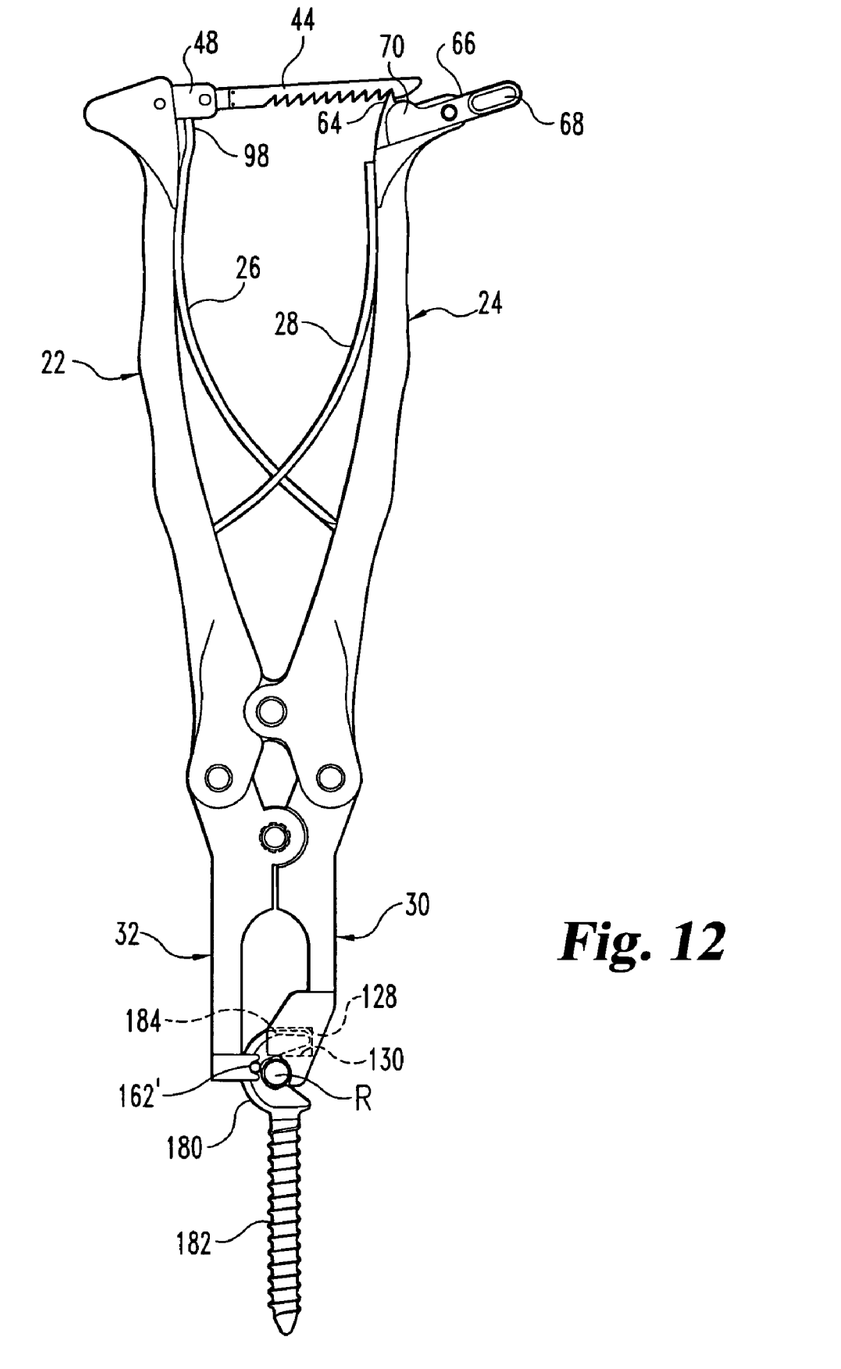
FIG. 12 is a side view of the embodiment shown in FIG. 11 in relation to a reduced orthopedic rod.

Once the rod is adjacent an implant into which the rod is to be placed or seated, instrument 20 may be introduced to reduce or force the rod into the implant. With handle portions 22 and 24 in an unstressed state, i.e. biased away from each other or otherwise spread apart, distal ends 112 and 142 of arm portions 30 and 32 are also spread apart. Distal ends 112 and 142 are placed around the combination of rod R and receiver member 180, so that distal end 112 is adjacent to or abutting a surface of rod R relatively distant from receiver member 180, and distal end 142 is adjacent to or abutting a surface of receiver member 180 relatively distant from rod R. In the embodiment in which distal end 142 includes protrusion(s) 162, such protrusion(s) 162 are inserted or maneuvered into hollow(s) or aperture(s) in receiver member 180. In an alternative embodiment in which receiver member 180 includes one or more side protrusions rather than hollow(s), distal end 142 may be provided with one or more hollows 162', e.g. in extensions 154 and/or 156, to accommodate such protrusions.

Where protrusion(s) 162 or hollow(s) 162' are provided and are substantially rounded or cylindrical and fit with corresponding parts of receiver member 180, as previously described, instrument 20 can pivot or rotate with respect to receiver member 180, as seen in one example in FIGS. 11-12. In that example, a distal portion of arm 32 changes angle with respect to the anchor or implant, as in FIG. 11 that portion of arm 32 is at an oblique angle with respect to engaging portion 182, and in FIG. 12 that portion of arm 32 is substantially parallel to engaging portion 182. The axis of rotation in that example substantially corresponds with protrusion(s) 162 or hollow(s) 162', and is different from the axes around which arms 22, 24, 30 and 32 pivot. Such pivoting or rotation around protrusion(s) 162 or hollow(s) 162' may force rod R generally toward the bone (downward as seen in FIG. 11) and/or generally toward receiver member 180. Such pivoting or rotation can occur in this embodiment as may be necessary for rod reduction.

Handle portions 22 and 24 are then squeezed together, which as discussed above forces distal ends 112 and 142 of arm portions 30 and 32 toward each other. Forcing together distal ends 112 and 142 causes rod R and receiver member 180 to move relative to each other so that they become nearer to each other. In many cases, the rod will undergo all or substantially all of such relative movement, and the implant (which is anchored to a bone) will remain relatively stationary. However, it will be appreciated that in some uses the surgeon would prefer the bone and implant to undergo movement toward the rod, for example in some cases of significant vertebral misalignment, and thus instrument 20 can cause such movement of the implant, perhaps with direct manipulation of the bone by the surgeon.

Squeezing of handle portions 22 and 24 is continued until distal ends 112 and 142 of arm portions 30 and 32 force rod R and receiver member 180 together to the extent desired by the surgeon. Toothed bar 44 and pawl 64 interact to maintain handle portions 22 and 24 (and thus arm portions 30 and 32) in a squeezed state, and keeping them from being biased apart if the surgeon's grip should loosen. In this way, instrument 20 can maintain pressure on a rod and implant while the surgeon rests his or her hand or performs another task. As rod R enters receiver member 180, distal end 112 of arm portion 30 approaches the implant, and specifically branches 184 on either side of channel 183 or other area that accommodates the rod. Distal end 112 of arm portion 30 is configured to be able to force rod R into receiver member 180 to the greatest degree desired, because cross pieces 128 and 130 are spaced apart so as to interfere minimally or not at all with branches 184 of receiver member 180. Thus, as distal end 112 approaches branches 184 of receiver member 180, branches 184 enter the gaps between cross pieces 128 and 130, allowing distal end 112 to press the rod toward or to the back of the implant, if that is desired. Through such squeezing of instrument 20 or pivoting of instrument 20 with respect to receiver member 180, or a combination of the two motions, rod R is reduced into channel 183 of receiver member 180.

Once the rod is positioned as the surgeon desires in the implant, the rod is locked into the implant using structure (e.g. set screw, cap, clamp) provided with the implant. Instrument 20 may be removed from contact with the rod and the implant after such locking, or before if the rod will remain at least approximately in the position desired by the surgeon. When it is desired to remove or loosen the contact of instrument 20 with the rod and/or the implant, the surgeon may press lever 68, which pivots to push toothed bar 44 away from pawl 64. Springs 26 and 28 then act to push handle portions 22 and 24 apart, per their normal bias, and distal portions 112 and 142 of arm portions 30 and 32 come away from the rod and the implant. The surgeon may then move to reduction of the rod into another implant, or may remove instrument 20 from the surgical site to perform other tasks or conclude the surgical procedure.

The anchors and connecting member may be positioned in or along one or more parts of the spine, including the cervical, thoracic, lumbar and/or sacral portions. Although the use of instrument 20 is described in the above context, instrument 20 could be used with a variety of screws, hooks or other fixation implants, or in connection with orthopedic implants in parts of the body other than the spine.

The above embodiment may be made of stainless steel, certain hard plastics, or other materials that are compatible with surgical procedures and the implants and rods with which instrument 20 is used.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A rod reducing instrument comprising:

first and second handle elements each having a proximal portion and a distal end, said handle elements being pivotally connected to each other adjacent said distal ends of said handle elements, at least one spring connected to at least one of said handle elements and between said handle elements, whereby said handle elements are biased apart;

first and second arm elements each having a proximal end and a distal end, said arm elements being pivotally connected to each other between said ends, said proximal end of said first arm element being pivotally connected to said distal end of said first handle element, and said proximal end of said second arm element being pivotally connected to said distal end of said second handle element, whereby bringing together said first and second handle elements;

said distal end of said first arm element having a substantially U-shaped portion, said U-shaped portion having two extension portions substantially parallel to said first arm element and a cross-piece joining said extension portions, said U-shaped portion connecting to the remainder of said first arm element adjacent one or both of said cross-piece and one of said extension portions whereby said U-shaped portion is laterally offset from the rest of said first arm element, said extension portions having respective distal ends, said distal ends of said extension portions each including a protrusion, said protrusions substantially facing each other;

said distal end of said second arm element having a substantially U-shaped portion, said U-shaped portion having two extension portions substantially parallel to said second arm element and a pair of cross-pieces joining said extensions portion, said U-shaped portion connecting to the remainder of said second arm element adjacent one or both of one of said cross-pieces and one of said extension portions whereby said U-shaped portion is laterally offset from the rest of said second arm element, said extension portions of said second arm having respective distal ends, said distal ends of said extension portions each including a substantially part-cylindrical hollow, said hollows being substantially coaxial and having a radius equal to or larger than the radius of a spinal rod.

2. The apparatus of claim 1, further comprising an elongated toothed member connected to one of said handle elements and a pawl connected to the other of said handle elements, said toothed member and said pawl positioned so that they interact to hold said handle elements against movement away from each other.

3. The apparatus of claim 2, further comprising a lever having a handle and a contact portion, said lever being connected adjacent said pawl to the handle element to which the pawl is connected, and positioned so that said contact portion of said lever is adjacent said toothed bar, whereby pressing said handle of said lever causes said contact portion of said lever to push against said toothed bar and disengage said toothed bar from said pawl.

4. The apparatus of claim 2, wherein said toothed bar is pivotably attached to said one of said handle portions via a post having a slot, and further comprising:
 a leaf spring attached to the handle element to which said toothed bar is attached and positioned between said handle elements, said leaf spring having a portion that is adjacent said toothed bar and at least partially within said slot, whereby said toothed bar is biased relatively toward said pawl.

5. The apparatus of claim 1, wherein said apparatus is used in conjunction with an orthopedic bone anchor having two spaced branches, and said cross-pieces are separated by a gap sufficient to admit one of said branches.

6. The apparatus of claim 1 wherein one of said cross-pieces is more proximal to said handle portions and one of said cross-pieces is more distal from said handle portions, and said more distal cross-piece includes a tab portion.

7. The apparatus of claim 6, wherein said tab portion is at least partially curved.

8. The apparatus of claim 1, wherein said U-shaped portion of said second arm element is angled toward said first arm element.

9. The apparatus of claim 8, wherein said second arm element has a longitudinal axis, and the angle between said axis and said U-shaped portion of said second arm element is about 160 degrees.

10. A rod reduction system comprising:
 an orthopedic implant having two spaced apart branches defining a channel therebetween sized to receive an orthopedic rod;
 a first arm portion adapted to connect to the orthopedic rod, said arm portion including two extensions, two cross-pieces substantially perpendicular to said extensions and forming a gap between them, and said extensions each having a hollow for accommodating the orthopedic rod;
 a second arm portion adjacent said first arm portion, said second arm portion being adapted to connect to the orthopedic implant, said second arm portion including two extensions and a cross-piece substantially perpendicular to said extensions, each of said extensions of said second arm including one of a protrusion and a hollow for connecting to the orthopedic implant;
 whereby said arm portions are operable to force the orthopedic rod and the orthopedic implant together wherein one of the branches of the orthopedic implant is positioned within said gap between said two cross-pieces of said first arm when the orthopedic rod is positioned within the channel, wherein one of said cross-pieces of said first arm portion is more proximal to a user, and one of said cross-pieces is more distal from the user, and said more distal cross-piece includes a tab portion.

11. The apparatus of claim 10, wherein said hollow forms a substantially semi-circular section.

12. The apparatus of claim 10, further comprising an elongated toothed member and a pawl operatively linked to said arm portions, said toothed member and said pawl positioned so that they operate to inhibit said arm portions from movement away from each other.

13. The system of claim 10, wherein said first arm portion has a longitudinal axis, and the angle between said axis and said extensions of said first arm element is about 160 degrees.

14. The system of claim 10, further comprising:
 an elongated toothed member and a pawl operatively linked to said arm portions, said toothed member and said pawl positioned so that they operate to inhibit said arm portions from movement away from each other; and
 a lever having a handle and a contact portion, said lever being connected adjacent said pawl and positioned so that said contact portion of said lever is adjacent said toothed bar, whereby pressing said handle of said lever causes said contact portion of said lever to push against said toothed bar and disengage said toothed bar from said pawl.

15. The system of claim 10, wherein said first arm portion has a longitudinal axis, and both of said extensions of said first arm portion are on the same side of said axis of said first arm.

16. The system of claim 10, said second arm portion has a longitudinal axis, and both of said extensions of said first arm portion are on the same side of said axis of said second arm.

17. The system of claim 16, wherein said first arm portion has a longitudinal axis, and both of said extensions of said first arm portion are on the same side of said axis of said first arm.

18. The system of claim 10, further comprising:
 an elongated toothed member and a pawl operatively linked to said arm portions, said toothed member and said pawl positioned so that they operate to inhibit said arm portions from movement away from each other, wherein said toothed bar is spring-biased toward said pawl.

19. A rod reduction system, comprising:
 an orthopedic implant comprising a rod receiver member including a channel sized to receive an orthopedic rod, said channel at least partially formed by a branch; and
 a rod reduction instrument comprising:
  a first arm portion adapted to connect to said rod, said arm portion including two extensions, two cross-pieces substantially perpendicular to said extensions and forming a gap between them, wherein said gap is wide enough to allow said branch of said orthopedic implant to at least partially pass through, and said extensions each having a hollow for accommodating said rod;
  a second arm portion adjacent said first arm portion, said second arm portion being adapted to connect to said orthopedic implant, said second arm portion including two extensions and a cross-piece substantially perpendicular to said extensions, each of said extensions of said second arm including one of a protrusion and a hollow for connecting to said orthopedic implant;
 whereby said arm portions are operable to force the orthopedic rod into said channel of said orthopedic implant wherein said branch of said orthopedic implant is positioned within said gap between said two cross-pieces of said first arm when the orthopedic rod is positioned within said channel.

20. The system of claim 19, wherein said first arm portion has a longitudinal axis, and both of said extensions of said first arm portion are on the same side of said axis of said first arm.

21. The system of claim 19, wherein said second arm portion has a longitudinal axis, and both of said extensions of said first arm portion are on the same side of said axis of said second arm.

22. The system of claim 21, wherein said first arm portion has a longitudinal axis, and both of said extensions of said first arm portion are on the same side of said axis of said first arm.

23. A rod reduction instrument comprising:
 a first arm portion adapted to connect to an orthopedic rod, said arm portion including two extensions, two cross-pieces substantially perpendicular to said extensions and forming a gap between them, and said extensions each having a hollow for accommodating the orthopedic rod;

a second arm portion adjacent said first arm portion, said second arm portion being adapted to connect to an orthopedic implant having two spaced apart branches, said second arm portion including two extensions and a cross-piece substantially perpendicular to said extensions, each of said extensions of said second arm including one of a protrusion and a hollow for connecting to the orthopedic implant; and wherein said extensions of said first arm portion are fixed and noncompressible with respect to each other, and said extensions of said second arm portion are fixed and noncompressible with respect to each other; and whereby said arm portions are operable to force an orthopedic rod and an orthopedic implant together.

24. The apparatus of claim 23, wherein said first arm portion has a longitudinal axis, and both of said extensions of said first arm portion are on the same side of said axis of said first arm.

25. The apparatus of claim 23, wherein said second arm portion has a longitudinal axis, and both of said extensions of said first arm portion are on the same side of said axis of said second arm.

26. The apparatus of claim 25, wherein said first arm portion has a longitudinal axis, and both of said extensions of said first arm portion are on the same side of said axis of said first arm.

27. A rod reduction instrument comprising:

a first arm portion adapted to connect to an orthopedic rod, said arm portion including two extensions, two cross-pieces substantially perpendicular to said extensions and forming a gap between them, and said extensions each having a hollow for accommodating the orthopedic rod;

a second arm portion adjacent said first arm portion, said second arm portion being adapted to connect to an orthopedic implant having two spaced apart branches, said second arm portion including two extensions and a cross-piece substantially perpendicular to said extensions, each of said extensions of said second arm including one of a protrusion and a hollow for connecting to the orthopedic implant;

whereby said arm portions are operable to force an orthopedic rod and an orthopedic implant together, and wherein one of said cross-pieces of said first arm is adjacent said hollows of said extensions and includes a tab portion that is at least partially curved, said curve being configured approximately the same as said hollows.

28. The apparatus of claim 27, wherein said first arm portion has a longitudinal axis, and both of said extensions of said first arm portion are on the same side of said axis of said first arm.

29. The apparatus of claim 27, wherein said second arm portion has a longitudinal axis, and both of said extensions of said first arm portion are on the same side of said axis of said second arm.

30. The apparatus of claim 29, wherein said first arm portion has a longitudinal axis, and both of said extensions of said first arm portion are on the same side of said axis of said first arm.

31. The apparatus of claim 27, wherein said extensions of said first arm portion are angled toward said second arm portion.

32. The apparatus of claim 31, wherein said first arm portion has a longitudinal axis, and the angle between said axis and said extensions of said first arm portion is about 160 degrees.

33. A rod reduction instrument comprising:

a first arm portion adapted to connect to an orthopedic rod, said arm portion including two extensions, two cross-pieces substantially perpendicular to said extensions and forming a gap between them, and said extensions each having a hollow for accommodating the orthopedic rod;

a second arm portion adjacent said first arm portion, said second arm portion being adapted to connect to an orthopedic implant having two spaced apart branches, said second arm portion including two extensions and a cross-piece substantially perpendicular to said extensions, each of said extensions of said second arm including one of a protrusion and a hollow for connecting to the orthopedic implant, whereby said arm portions are operable to force an orthopedic rod and an orthopedic implant together, wherein said extensions of said first arm portion are angled toward said second arm portion;

an elongated toothed member and a pawl operatively linked to said arm portions, said toothed member and said pawl positioned so that they operate to inhibit said arm portions from movement away from each other; and a lever having a handle and a contact portion, said lever being connected adjacent said pawl and positioned so that said contact portion of said lever is adjacent said toothed bar, whereby pressing said handle of said lever causes said contact portion of said lever to push against said toothed bar and disengage said toothed bar from said pawl.

34. The apparatus of claim 33, wherein one of said cross-pieces of said first arm portion is more proximal to a user, and one of said cross-pieces is more distal from the user, and said more distal cross-piece includes a tab portion.

35. The apparatus of claim 33, wherein said first arm portion has a longitudinal axis, and the angle between said axis and said extensions of said first arm portion is about 160 degrees.

36. A rod reduction instrument comprising:

a first arm portion adapted to connect to an orthopedic rod, said arm portion including two extensions, two cross-pieces substantially perpendicular to said extensions and forming a gap between them, and said extensions each having a hollow for accommodating the orthopedic rod;

a second arm portion adjacent said first arm portion, said second arm portion being adapted to connect to an orthopedic implant having two spaced apart branches, said second arm portion including two extensions and a cross-piece substantially perpendicular to said extensions, each of said extensions of said second arm including one of a protrusion and a hollow for connecting to the orthopedic implant, whereby said arm portions are operable to force an orthopedic rod and an orthopedic implant together, wherein said extensions of said first arm portion are angled toward said second arm portion; and an elongated toothed member and a pawl operatively linked to said arm portions, said toothed member and said pawl positioned so that they operate to inhibit said arm portions from movement away from each other, wherein said toothed bar is spring-biased toward said pawl.

37. The apparatus of claim 36, wherein one of said cross-pieces of said first arm portion is more proximal to a user, and one of said cross-pieces is more distal from the user, and said more distal cross-piece includes a tab portion.

38. The apparatus of claim 36, wherein said first arm portion has a longitudinal axis, and the angle between said axis and said extensions of said first arm portion is about 160 degrees.

* * * * *

UNITED STATES PATENT AND TRADEMARK OFFICE
CERTIFICATE OF CORRECTION

PATENT NO. : 7,625,376 B2  Page 1 of 1
APPLICATION NO. : 11/043318
DATED : December 1, 2009
INVENTOR(S) : Brumfield et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 929 days.

Signed and Sealed this

Twenty-sixth Day of October, 2010

David J. Kappos
*Director of the United States Patent and Trademark Office*